United States Patent [19]

Pyatt et al.

[11] Patent Number: 4,527,122
[45] Date of Patent: Jul. 2, 1985

[54] BORE HOLE DIRECTION MEASURING INSTRUMENT CONTROL

[76] Inventors: Lawrence A. Pyatt, 260 Princess Ann Ct., Henderson, Nev. 89015; Robert W. Thompson, 5210 Ensley Dr., Riverside, Calif. 92505

[21] Appl. No.: 387,598

[22] Filed: Jun. 11, 1982

Related U.S. Application Data

[60] Division of Ser. No. 119,171, Feb. 6, 1980, Pat. No. 4,365,197, which is a continuation-in-part of Ser. No. 892,284, Mar. 31, 1978, abandoned.

[51] Int. Cl.³ .................... G01N 27/82; G03B 37/00; G01D 9/42; G01R 33/00
[52] U.S. Cl. .................................. 324/226; 324/221; 354/63; 346/107 W
[58] Field of Search ............... 324/219, 220, 221, 226; 166/66, 255; 307/116; 346/107 W, 33 W; 354/63; 175/45; 33/314

[56] References Cited

U.S. PATENT DOCUMENTS

| | | | |
|---|---|---|---|
| 2,250,703 | 7/1941 | Crites et al. | 324/221 X |
| 2,698,920 | 1/1955 | Gieshe | 166/66 |
| 3,243,697 | 3/1966 | Schmidt | 324/221 |
| 3,546,478 | 12/1970 | Lindsey | 307/116 |
| 4,171,578 | 10/1979 | Meador | 346/107 W |

*Primary Examiner*—Gerard R. Strecker
*Assistant Examiner*—Walter E. Snow
*Attorney, Agent, or Firm*—Grover A. Frater

[57] ABSTRACT

A combination of magnetics and a special geometric environment is employed to distinguish whether an instrument is positioned within a pipe formed of magnetizable or non-magnetizable material, and is the basis, in part, for a method and an apparatus used in controlling picture taking at the bottom of a well bore. A coil is energized repetitively in a circuit in which the voltage across the coil, or the current that flows through the coil, can be measured. Whether the coil is in a magnetic or non-magnetic environment is determined by the magnitude of the change in coil voltage or current.

2 Claims, 6 Drawing Figures

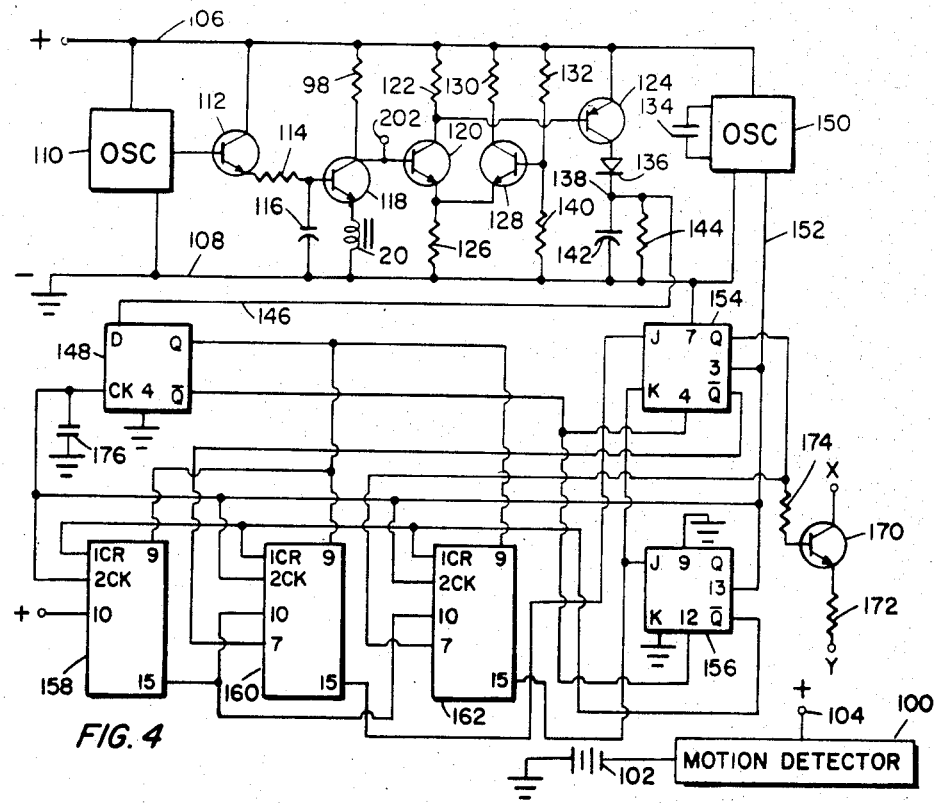
FIG. 4
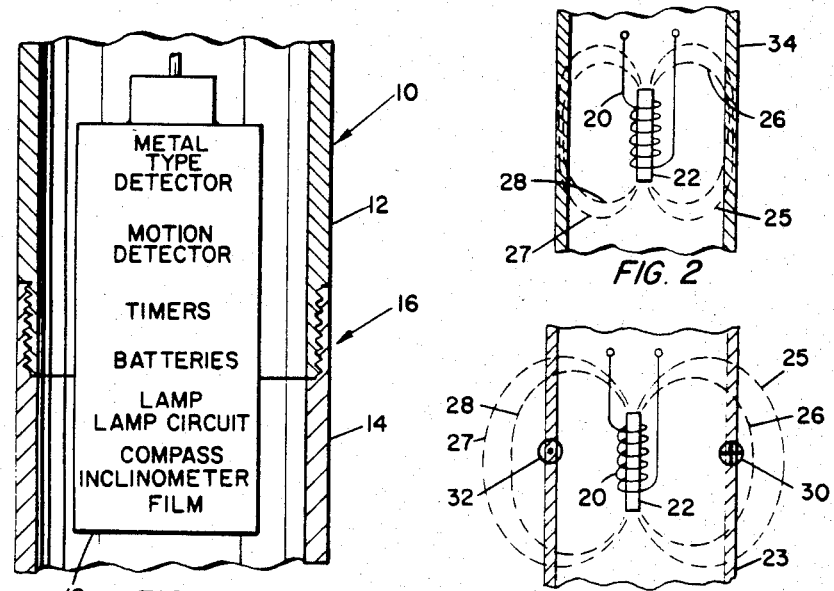
FIG. 1
FIG. 2
FIG. 3

BORE HOLE DIRECTION MEASURING INSTRUMENT CONTROL

CROSS-REFERENCE TO RELATED APPLICATION

This application is a division of earlier application Ser. No. 119,171, filed Feb. 6, 1980, now U.S. Pat. No. 4,365,197, which is a continuation-in-part of application Ser. No. 892,284, filed Mar. 31, 1978, now abandoned.

TECHNICAL FIELD

This invention relates to methods and means for determining whether a metallic enclosure, in particular a drill pipe, is made of magnetic or non-magnetic material, and it relates to an instrument having that capability for controlling illumination of the light source in the photographing of compasses at the bottom of drilled wells.

BACKGROUND ART

While not limited to that application, the invention is particularly useful in connection with the taking of photographic pictures of a compass, or inclinometer, or both, at the bottom of a well bore. Well drillers can control the direction of deep wells by control of the drilling tools. But control is accomplished in terms of adjustment to change from current direction as drilling proceeds. That means that the driller must know the wells' current direction from time to time. Current direction is determined by lowering a compass inclinometer to the bottom of the well and then photographing the compass assembly to record its direction in azimuth and inclination. The task of photographing a compass at the bottom of a well is both complicated and expensive.

The compass needle is acted on by the earth's magnetic field. To permit that, the compass must be disposed in a non-magnetic section of pipe at the time that the photograph is taken. Current practice is to include a short length of non-magnetic pipe at or near the lower end of the drill pipe. That length of pipe is ordinarily made of Monel and it is called a "collar." The compass must be disposed in that section when it is photographed. Care must be taken to ensure that the compass assembly is not in motion at the time that the photograph is taken. Current practice is to include a detector which detects absence of motion and a means for precluding exposure of the film for some selected time interval measured from the last action which could cause movement of the compass needle.

To prevent premature exposure, it has been necessary to ensure that instrument motion does not stop until the instrument has reached the position at which the photograph is to be taken. To overcome that requirement, a conventional clock has been used so that photograph taking occurs at some fixed time after the clock is started at the well head. That solution is subject to failure if, for any reasonn the time required to lower the instrument is other than the predicted time.

This invention relates to the problem of ensuring that the compass is in the non-magnetic collar and to the problem of postponing picture taking until the compass needle has "settled down" before the film is exposed. To lower the apparatus into, and to retrieve if from, a deep well is very costly. It is important to be able to determine reliably and with a high degree of certainty whether the compass is, or is not, in the non-magnetic section of the drill pipe.

DISCLOSURE OF THE INVENTION

It is an object of the invention to provide an imporved method for controlling photograph taking in wells.

A related object is to ensure that picture taking is accomplished at a selected point in a well, and, in this connection, to provide an improved apparatus for detecting the presence of metal and, particularly, whether that metal is or is not a magnetic section of a pipe.

It is an object of the invention to provide an improved method related to deep well photography by which to determine whether there is or is not a magnetizable body in the vicinity of a selected spacial position and, in particular, to determine whether a given point along a well is within a pipe of magnetic or non-magnetic material.

These and other objects and advantages of the invention are realized, in part, by the provision of a coil which is energizable to create a magnetic field and of a means for holding the coil within an enclosure such that the field of the coil will be substantially confined by the enclosure, in the event that the enclosure is made of non-magnetizable conductive material, and which will induce substantial circulating currents, enough to present a heavy load permitting current flow in the coil in excess of the current that would flow if the coil was located in free space, in the event that the enclosure is made of magnetizable but electrically conductive material.

That kind of a coil is used in conjunction with a means for measuring the voltage across, or the current through, the coil when energized. The voltage or current is indicative of whether the coil is disposed in a magnetic or non-magnetic pipe or other enclosure, and it is used to develop an indicating signal which indicates the nature of the enclosure. In preferred form, the coil is energized through a transistor whose control electrode is subjected to a periodically varying voltage wave form.

It is a feature to change from analog to digital measurement by switching if the voltage or current excursion exceeds some value that indicates that the coil is in one kind of enclosure and not the other. It is another feature to house the coil in a non-magnetic casing in which case the instrument can detect when it is in a magnetic environment and in a non-magnetic environment.

It is a further feature to use the indicating signal to control initiation of interrelated timing circuits.

These and other features and advantages of the invention will become clear upon a reading of the specification which follows.

BRIEF DESCRIPTION OF THE DRAWINGS

In the drawings

FIG. 1 is a schematic representation of an instrument in which the invention is embodied in a section of drill pipe shown in cross-section;

FIG. 2 is a diagram illustrating part of the operation of the invention when detecting pipe of magnetic material;

FIG. 3 is a diagram illustrating part of the operation of the invention when detecting pipe of non-magnetic but metallic material;

FIG. 4 is a circuit diagram of a preferred embodiment of the invention; and

DESCRIPTION OF THE PREFERRED EMBODIMENT

Figure 5:
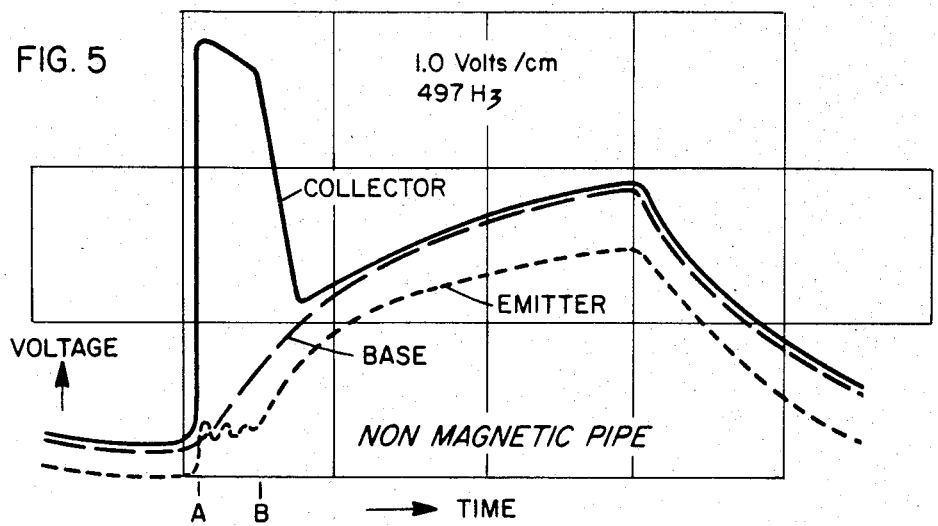
FIGS. 5 and 6 are diagrams of the wave shapes at the terminals of the sensing transistor when the sensing coil is in non-magnetic pipe, in the case of FIG. 5, and in magnetic pipe in the case of FIG. 6.

In FIG. 1, the numeral 10 designates a section of drill pipe including a fragment of the lower end of a magnetic steel pipe 12 and a fragment of the upper end of a pipe 14 of non-magnetic metal. The two are interconnected at threaded region 16. Disposed within the pipe is an instrument 18 whose purpose is to photograph the position of a compass assembly on a film.

Sometimes the compass serves as an inclinometer as well as a compass, and in some cases a separate inverted plumbob is added to indicate inclination. Those elements form no part of the invention, nor does the film which is placed on one side of the compass and inclinometer combination, or the lamp that is placed on the other side. The invention is concerned with illumination of the lamp and with illuminating the lamp only when the compass is in the non-magnetic, metallic portion of the pipe, after sufficient time has elapsed to allow the compass needle to become steady.

To perform those several functions, the instrument of the preferred embodiment includes a metal type detector, timers, a power source in the form of batteries, lamp, lamp circuit, a compass and inclinometer, and a film. In the preferred form, these elements are housed in a non-magnetic case which may be formed of electrically conductive material such, for example, as Monel metal. The diagram of FIG. 4 includes the batteries, metal type detector, timers, and terminals for connection to the lamp circuit. The metal type detector includes a sensing coil 20 and its operation will be explained in connection with FIGS. 2 and 3.

In preferred form, the sensing coil 20 is wound about a straight elongated form, preferably about an elongated ferrite core. It is housed in the instrument case 18 so that the axis of the coil is parallel to, and preferably coincident with, the axis of case 18. The case is arranged so that its axis can be expected to be substantially parallel with the axis of the drill pipe. The requirement, in the preferred embodiment, is that the axis of the coil be more parallel than transverse to the axis of the drill pipe. The reason for that arrangement is explained in connection with FIG. 3.

In FIG. 3, the coil and its core 22 are disposed within a Monel pipe 23. When current flows through the coil, a magnetic field is established around the coil. That field is represented, in accordance with convention, by closed loops 25, 26, 27 and 28 shown as dashed lines which extend through the core, and then as dashed lines which extend through the core, and then out at one end and around and back into the core at the opposite end. No loop crosses any other according to convention. Since the permeability of Monel is near unity, the flux lines pass through the pipe walls in a pattern similar to what would be expected in air. As the flux field builds, the flux lines "cut" the pipe wall and that movement of magnetism interacts with the free electrons in the electrically conductive pipe to cause a motion of those electrons according to the right-hand rule. The electrons flow around the circumference of the pipe so that the pipe acts as a single "shorted" turn secondary winding of large cross-sectional area. The resistance of the pipe is low so that it presents a heavy load to the primary winding 22 which draws a heavy current. Current flow is represented in FIG. 3 by the "flow away" and "flow toward" symbols 30 and 32, respectively.

Returning to FIG. 4, the coil 20 is in series with the emitter-collector circuit of a transistor 118 and a load resistor 98. The transistor is cut off during part of each cycle so the result is a large current change and a large voltage change at the collector of transistor 118 when the coil 20 is in Monel pipe.

If the coil 20 was oriented so that its axis was normal to the pipe axis, the flux direction would be changed by 90 degrees and so would the direction of the induced current. The current would flow in the longitudinal direction of the pipe and the pipe would act as a secondary winding in much lesser degree determined primarily by dissymmetry in the magnetic field.

Sensitivity is also effected by conductivity of the protective case 18. That case must be made of non-magnetic material so that the magnetic field will not be confined to the case but can reach the pipe. Sensitivity of the instrument is reduced in the sense that a portion of the current change in the coil results from current flow in the case. However, it will be seen that that effect does not lessen ability of the instrument to distinguish steel pipe from a non-magnetic pipe.

Magnetic lines of flux follow the path of least reluctance, and when the coil 20 is disposed within a pipe 34 of magnetic material, the flux lines will extend from one end of core 22 through the non-magnetic case of instrument 18 into and along the magnetic pipe and then back through the case of instrument 18 to core 22. There will be less "cutting" of the pipe by flux lines. A current will be induced in the pipe wall as it was in the Monel pipe of FIG. 3, but higher resistance, eddy currents and other losses and phase stifling effects serve to minimize that current. Further, the greater magnetic efficiency in the magnetic circuit results in a stronger field, collapse of more flux when transistor 118 cuts off current, and it creates a greater counter-electromotive force in coil 20. The result is a lesser current swing. That is true notwithstanding the circulating current around the case of instrument 18 and the load it represents.

The end result is that presence of coil 20 within the steel pipe results in a magnetic action which produces a counter-electromotive force in the coil and an opposition to current change which substantially nullifies the effect of the instrument case as a shorted turn. There is no such nullification when the instrument is housed in a non-magnetic pipe so current change is large whether it be the result of the instrument case or the pipe, or both, acting as a shorted turn.

There is another effect to be accounted for. Lenz's Law describes that counter-electromotive force has a magnitude that depends upon the rate of change of magnetic flux. At very low frequencies, the counter-electromotive force opposing flow in coil 20 is very low notwithstanding that the coil is disposed within the steel portion of the pipe. Thus, at very low frequencies, the signal output at the collector of transistor 118 will be relatively high when the coil is housed in steel. That signal strength diminishes rapidly when the frequency is increased. An opposite effect occurs at low frequencies when the coil 20 is disposed in the Monel portion of the pipe. At low frequencies the flux change is slow and the magnitude of the circulating current in the "shorted turn" pipe is small. That means that the load is small and the self-inductance of coil 20 is adequate to limit current flow. Accordingly, the voltage excursion at the collector of transistor 118 is relatively small. However, the signal magnitude increases rapidly with frequency. In an actual circumstance, the non-magnetic collar has an inside diameter of about three inches and a wall thickness greater than one inch. The instrument case has an outside diameter of about two inches and a wall thickness on the order of one-quarter inch. The lower frequency limit for operation of the instrument will be about 300 cycles. At frequencies below that, it becomes impossible to distinguish Monel from steel, or the results are unreliable. As frequency is increased above 300 cycles per second, the differential in magnitude between the signal in steel and the signal in Monel is increased until some optimum frequency is reached. For the dimensions given, that frequency will fall in the range of 400 to 800 cycles per second. Above that, the current variation in coil 20 is diminished when the coil is disposed in Monel. The effect of self-inductance in the coil overtakes the effect of the heavy loading so that at about 800 cycles per second, for the values given, the magnitude of the signal is reduced to the point where detection becomes difficult and unreliable. Accordingly, there is a frequency window in which the metal type detector must be operated. That window can be shifted by changing the characteristics of the coil 20, but the preferred embodiment employs the component values listed below, and a frequency of operation between 400 and 600 cycles per second. In the particular case shown, the frequency is 500 cycles per second.

At the upper portion of FIG. 4, line 106 is connected to positive terminal 104 and power line 108 is connected to ground. The circuit includes an oscillator 110 whose frequency is relatively low, and it need comprise no more than a series of three inverters and some feedback resistors and a capacitor. Its output is connected to the base of NPN transistor 112. Its collector is connected to the positive line 106. Its emitter is connected to ground through the series combination of a resistor 114 and an electrolytic capacitor 116. The junction of the resistor and the capacitor is connected to the base of a NPN transistor 118 whose collector is connected to the positive line 106 through resistor 98, mentioned earlier. The emitter of the transistor is connected through the sensing coil 20 to ground line 108. The output of transistor 118 is taken from its collector and applied to the base of an NPN transistor 120 whose collector is connected to the positive line through a load resistor 122 and to the base of an PNP transistor 124. The emitter of transistor 120 is connected to ground through resistor 126, and it is connected to the emitter of a transistor 128 whose collector is connected to the positive line through load resistor 130. The base of transistor 128 is connected to the junction between two resistors, 132 and 140, which are connected between the positive line and the negative line in series, in that order. The emitter of transistor 124 is connected to the positive line 106 and its collector is connected through a diode 136 to a line 138. A capacitor 142 and a resistor 144 are connected in parallel between line 138 and the negative line 108. Another output line 146 is connected from line 138 to the "D" input terminal of a D-type flip-flop 148.

Except for the D-type flip-flop, the circuit thus far described is the metal type detector. Its function is to apply a positive signal to the D terminal of the flip-flop when coil 20 is located within the Monel section of the pipe and to apply a negative signal to the D input of flip-flop 148 when the sensing coil 20 is located within a steel portion of the drill pipe. To do that, the output of oscillator 110 is applied to the base terminal of amplifier 112. Current flowing through the collector-emitter circuit of the transistor flows through resistor 114 to charge capacitor 116. The capacitor discharges through the base-emitter circuit of the following transistor 118. The result is the application to the base of transistor 118 of the voltage that appears across capacitor 116. That input voltage causes a corresponding flow of current in the emitter-collector circuit of transistor 118, except as that current flow, and counter-electromotive force, develops an opposing voltage across the sensing coil 20 in the manner previously described. The output signal of that transistor is applied to the base of transistor 120 whose bias is controlled by current flow through transistor 128. The baseof the latter is biased to a fixed value by the voltage divider formed by the combination of resistors 132 and 140. Current flowing through the transistor 128 flows through resistor 126 in the emitter circuit of transistor 120. Only when the base voltage of the transistor exceeds a value determined by the voltage across resistor 126 does current flow in transistor 120. The output of that transistor is taken from its collector and applied to the base of switching transistor 124 which, when turned on, permits current flow through the diode 136 into capacitor 142 so that the output line 138 becomes positive. The capacitor is discharged through resistor 144. The effect is that line 146 will remain positive while the coil 20 is disposed within the Monel collar, but the line will return to its negative state when the coil 20 is disposed within the steel pipe. In the latter case, the voltage at the base of transistor 120 is insufficient, in view of the voltage across resistor 126, to permit current flow through transistor 120 for the turning on of transistor 124. Accordingly, the charge on capacitor 142 will leak off through resistor 144 and line 146 will be returned to a low state and will remain low.

The edge clocked flip-flop 148 initiates a counting and control cycle when a high signal is applied to its D input by line 146 from the output line 138. Clock signals for the digital portion of the circuit are generated in an oscillator 150 whose output signals are applied by a line 152 to the clock pins 3 and 13 of JK flip-flops 154 and 156, respectively. Clock signals are also applied to the clock pin CK of flip-flop 148 and to pin 2 of each of three counters, 158, 160 and 162. The counters are cleared and preset when a low signal is applied to their number 1 pins from the Q-bar output of flip-flop 156. Counting begins when a high signal is applied to the enable pin, number 9, of each of the counters from the Q output of flip-flop 148.

The circuit is arranged so that two counting functions are performed. Counters 158 and 162 are connected together as one counter called the exposure time counter, and counters 158 and 160 are connected together as a second counter called the settling time counter. The first of those counters is used to control the time during which the camera light source, the lamp, is illuminated. The second of the counters introduces a time delay between the time when coil 20 has sensed that it is disposed within the Monel section of pipe and the time when energization of the lamp excitation circuit is permitted. Output of the exposure time counter is taken from pin 15 of counter 162, and the output of the settling time counter is taken at pin 15 of the counter chip 160. Pin 15 of counter chip 162 is connected to the K input of flip-flop 154 and to the J input of flip-flop 156. The output of counter chip 160 at pin 15 is applied to the J input of counter 154.

Turning to the output end of the circuit, the lamp excitation circuit is connected to terminals X, Y at the right side of FIG. 4. Terminal X is at the collector of a switching transistor 170 whose emitter is connected to terminal Y through a resistor 172. The base of that transistor is connected through a resistor 174 to the Q output terminal of flip-flop 154. The transistor 170 is turned on to energize the lamp excitation circuit when the Q output of flip-flop 154 goes high. Q goes high at the clock signal if J is high and K is low.

The function of flip-flop 148 is to start the counters. The function of flip-flop 154 is to control turn-on and turn-off of transistor 170, and the function of flip-flop 156 is to reset the counters after completion of the settling time and the exposure time counts. The exposure counting does not begin until the settling time counter has completed its count and has furnished a high signal to the J input of flip-flop 154. That mode of operation can be achieved because the counters will not count while a low signal is applied to their pin 7. Pin 7 of the exposure time interval counter is driven by the Q output of flip-flop 154, and pin 7 of the settling time counter is driven by the Q-bar output of flip-flop 154.

The digital circuit operates as follows. Oscillator 150 generates clock signals which are applied to the clock inputs of the several digital devices. However, none of them count or change state until a positive signal appears on line 138 of the metal-type detector circuit and is applied to the D input pin of flip-flop 148. The flip-flop is then clocked so that the Q output goes high. That applies an enable signal to each of the three counter chips. The Q-bar output of flip-flop 148 goes low, and that signal is applied to the reset pins 4 and 12 of flip-flops 154 and 156, respectively. The counter has been cleared previously, so the count in counter 158 begins at "0." When that counter reaches maximum count, a high appears at pin 15 and that is applied to the count enable pins 10 of both of the counter chips 160 and 162. Flip-flop 154 has been reset. A high appears at the Q-bar terminal, and that is applied to pin 7 of counter 160 which is thereby enabled. A low is applied to pin 7 of counter 162 which is connected to the Q output of flip-flop 154. That means that the counter 162 is inhibited. When counter 160 reaches maximum count, a high signal appears at its pin 15 and that signal is applied to the J input of flip-flop 154. The K input of that flip-flop, and the J input of flip-flop 156 are low because they are connected to pin 15 of counter 162 which is inhibited. When counter 160 reaches its maximum count, a positive signal is applied to pin J of flip-flop 154 and that flip-flop changes state. A high appears at its Q output, thereby turning on the transistor 170 in the lamp excitation circuit and also enabling the counter 162. When counter 162 reaches full count, a positive signal from pin 15 of counter chip 162 is applied to the K input of flip-flop 154, and the J side of flip-flop 156. Flip-flop 154 resets and flip-flop 156 sets. Accordingly, the Q output of flip-flop 154 goes low to turn off the transistor 170 in the lamp excitation circuit. The Q-bar output goes high, terminating the signal to counter 160. The K input of the flip-flop 156 is at ground potential, so the appearance of a high at the end of the interval count at terminal J of flip-flop 156 changes its state so that a low appears at the Q-bar output. That low is applied to clear all of the counters.

The circuit of FIG. 4 is arranged so that a photograph will be taken automatically as soon as the compass photographing instrument is positioned so that coil 20 is within the Monel collar, and a time has elapsed sufficient to ensure that the compass assembly has stopped fluctuating.

In a representative circuit, the components may have the following values:

Transistors 112, 120, 118, 170 are type 2N3703;
Transistor 124 is type 2N3703;
D-type flip-flop 148 may be type MC 14013B;
Three counter chips are type MC 14163B;
Flip-flop 154 is type MC 14027B;
Flip-flop 156 is type MC 14584B;
Capacitor 176 has a value 0.01 mf;
Capacitor 142 has a value of 1 mf;
Capacitor 116 has a value of 2 mf;
Resistors 122, 130 and 144 are 100 K ohms;
Resistors 126 and 134 are 10 K ohms;
Resistor 114 has the value 300 ohms;
Resistor 98 has the value 2700 ohms.

The circuit uses six inverters packaged in chip MC 14069B. Three of those are connected in series to form oscillator 110, and the other three are connected in series to form oscillator 150. In each case, the first inverter in the series is connected in parallel with the series combination of a 1 megohm and a 2 megohm resistor. The junction between the two resistors is connected to the junction between the second and third inverters of the series through a capacitor which, in the case of oscillator 107, has the value 0.001 mf. The value of the capacitor in oscillator 150 is much larger. Oscillator 150 serves as the clock for the settling time counter and for the exposure time counter. The length of the settling time and exposure will depend upon the characteristics of the film and of the damping characteristics of the compass. Because of that, the value of the clock frequency controlling capacitor 134 is not specified and the counter-connections (number of counts) are not shown in the diagram. To select them in a given case requires no more than very ordinary skill. Settling time might be anything up to about 1.5 minutes, and the exposure time anything up to forty-five seconds, depending upon which ones are selected of the films and lamps and compasses that are currently in use.

The coil 20 has an inductance of about 233 microhenries. The core material of the coil is magnetic but is non-conductive. The frequency of oscillator 110 is at or near 500 Hz.

In some applications of the invention, when used as a metal detector, or in conjunction with other instruments, it may be desirable to work with analog signals, and, for that purpose, the preferred embodiment includes a terminal 202 at the collector of transistor 118. That terminal could be positioned at any point where the voltage or current variation in coil 20 can be measured, but the collector position is now preferred.

Experimentation with core materials for the coil has demonstrated that magnetic characteristics may vary greatly from sample to sample of commercially available ferrite core materials notwithstanding that they are described by the same or similar specifications. Use of certain pieces of a lot of cores operates to lower the optimum excitation frequency closer to 300 Hz than to the frequencies and ranges described above. Thus, merely by selection of cores it is possible to practice the invention with optimum results by energizing the core at frequencies in the range 200 Hz to 800 Hz.

The variation in the magnetic quality of ferrite cores now make it preferable to employ a core material which can be and is produced with qualties that fall reliably within a narrow range of values. Monel is such a material. While Monel is a brand name, it is applied to an alloy of nickel, copper and other constituents which are very well known. In the oil fields at least, the term "Monel" is used both as a brand name and as the generic term for alloys of the same general type. All are called "non-magnetic" although they exhibit magnetic qualties in some degree. Substitution of a Monel-type material, a "non-magnetic" but slightly magnetic metal, permits reduction of the core 22 by about half and lower optimum frequency to the range 275 Hz to 350 Hz. At the present time, the preferred embodiment of the invention employs such a core material. The ferrite core is no less useful than previously described, however, and the preferred excitation frequency remains in the range 200 to 800 cycles per second.

Figure 6:
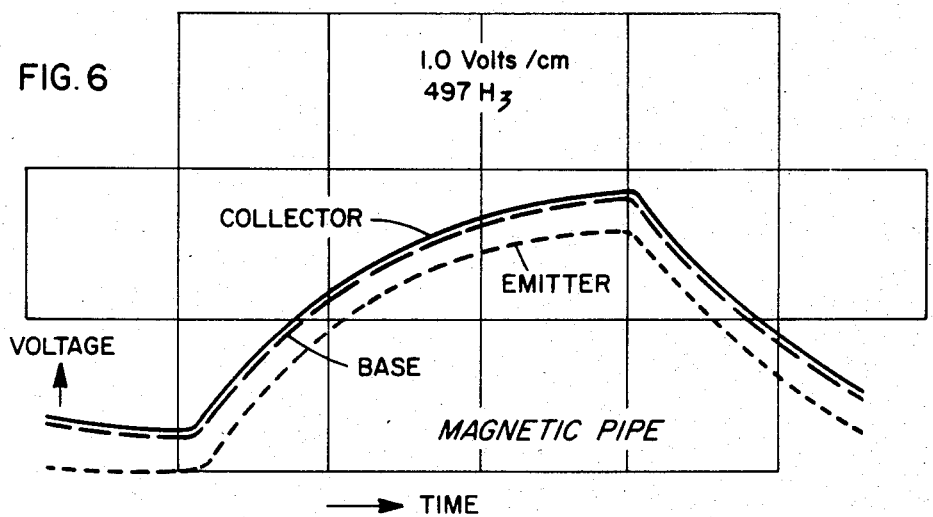

The preferred mode of detection and the detection circuit remain unchanged. FIG. 5 is a drawing of the voltage wave form at the base, collector and emitter of transistor 118 when the coil is in a non-magnetic metal pipe. FIG. 6 is a drawing of the voltage wave form at the base, collector and emitter of transistor 118 when the coil 20 is in a magnetic pipe.

In FIG. 5, phase shift resulting from the effect of loss of energy and self induction alters the voltage wave form at time A such that the base-emitter diode becomes reversed biased. The transistor is cut off and the collector voltage rises to a high value. The coil, which is in a non-magnetic environment, is seen to ring at its natural resonant frequency to delay the rise in emitter voltage. The ringing decays and emitter voltage rises. At time B, the base-emitter diode bias is reversed to allow conduction. As a consequence, collector voltage falls.

FIG. 6 describes the voltage relationships when the coil 20 is disposed in a magnetic section of pipe. In this case, there is no phase shift at the cycle beginning sufficient to reverse the bias of the base emitter junction and the transistor is not switched off. There is no sharp rise in collector voltage.

The phase shift in emitter voltage at the beginning of the cycle results from a combination of energy loss and self induction. Amplitude, and therefore relative amplitude of base and emitter voltage, is a function primarily of loss. Phase shift where there is loss is a function of frequency so the selection of a proper exciting frequency is necessary.

While a preferred embodiment of the invention has been described, other embodiments of the invention are possible. A list of variations would include changes in coil configuration, changes in the type of non-magnetic material in which the coil was housed, and changes in housing configuration and, of course, other changes are possible within the invention.

We claim:

1. The method of controlling photograph taking a selected position in a well bore with photographic equipment which comprises the steps of:
    (a) lowering the photographic equipment to said position and detecting when said photographic equipment is disposed at said position by detecting the character of the material surrounding the equipment at said position and while said equipment is stationary, detection of the character of the material surrounding the equipment at said position being accomplished by observing the effect of said material on a magnetic field which alternates at a frequency between 200 and 800 Hz;
    (b) initiating a clock timer only when said photographic equipment is disposed at said position; and
    (c) operating said photographic equipment at the end of a predetermined interval following initiation of said clock timer.

2. The method of controlling operation of photograph taking in a well bore to ensure that the subject of the photograph is in a substantially non-magnetic environment at the time of taking the photograph, which method comprises the steps of:
    (a) lowering photographic equipment and a photographic subject into the well with means for determining whether said photographic subject is in a magnetic or substantially non-magnetic environment;
    (b) determining with the aid of said means when said photographic subject is in a non-magnetic environment;
    (c) operating said photographic equipment to photograph said subject when the subject is in a non-magnetic environment; and
    (d) determining whether the environment is magnetic or non-magnetic being accomplished by observing the effect of said environment on a magnetic field which alternates at a frequency between 200 and 800 Hz.

* * * * *